US012692340B2

(12) United States Patent
Li et al.

(10) Patent No.: US 12,692,340 B2
(45) Date of Patent: Jul. 28, 2026

(54) AQUEOUS POLYURETHANE EMULSION FOR ULTRA-THIN POLYURETHANE CONDOM WITH LOW MODULUS AND HIGH STRENGTH, AND PREPARATION METHOD THEREFOR

(71) Applicant: Reckitt Benckiser Health Limited, Slough (GB)

(72) Inventors: Weihu Li, Suzhou (CN); Wenhe Guo, Lanzhou (CN); Baoling Zhu, Lanzhou (CN); Fei Wang, Suzhou (CN); Jiabing Dai, Lanzhou (CN)

(73) Assignee: Reckitt Benckiser Health Limited, Slough (GB)

( * ) Notice: Subject to any disclaimer, the term of this patent is extended or adjusted under 35 U.S.C. 154(b) by 910 days.

(21) Appl. No.: 17/787,171

(22) PCT Filed: Dec. 17, 2020

(86) PCT No.: PCT/CN2020/137262
§ 371 (c)(1),
(2) Date: Jun. 17, 2022

(87) PCT Pub. No.: WO2021/121323
PCT Pub. Date: Jun. 24, 2021

(65) Prior Publication Data
US 2023/0029922 A1 Feb. 2, 2023

(30) Foreign Application Priority Data
Dec. 19, 2019 (CN) .......................... 201911320711.6

(51) Int. Cl.
| | |
|---|---|
| C08G 18/12 | (2006.01) |
| A61F 6/04 | (2006.01) |
| C08G 18/08 | (2006.01) |
| C08G 18/32 | (2006.01) |
| C08G 18/34 | (2006.01) |
| C08G 18/40 | (2006.01) |
| C08G 18/42 | (2006.01) |
| C08G 18/48 | (2006.01) |
| C08G 18/50 | (2006.01) |
| C08G 18/66 | (2006.01) |
| C08G 18/73 | (2006.01) |
| C08G 18/75 | (2006.01) |

(52) U.S. Cl.
CPC ................ *C08G 18/12* (2013.01); *A61F 6/04* (2013.01); *C08G 18/0823* (2013.01); *C08G 18/0866* (2013.01); *C08G 18/3206* (2013.01); *C08G 18/3212* (2013.01); *C08G 18/3228* (2013.01); *C08G 18/348* (2013.01); *C08G 18/4018* (2013.01); *C08G 18/4238* (2013.01);

*C08G 18/4808* (2013.01); *C08G 18/4825* (2013.01); *C08G 18/4854* (2013.01); *C08G 18/5024* (2013.01); *C08G 18/6603* (2013.01); *C08G 18/6607* (2013.01); *C08G 18/6625* (2013.01); *C08G 18/6674* (2013.01); *C08G 18/6685* (2013.01); *C08G 18/6692* (2013.01); *C08G 18/73* (2013.01); *C08G 18/755* (2013.01); *C08G 18/758* (2013.01)

(58) Field of Classification Search
CPC ....... A61F 6/04; C08G 18/12; C08G 18/0866; C08G 18/3206; C08G 18/3212; C08G 18/348; C08G 18/4854; C08G 18/5024; C08G 18/6603; C08G 18/6625; C08G 18/0823; C08G 18/3228; C08G 18/4238; C08G 18/4825; C08G 18/73; C08G 18/758; C08G 18/755; C08G 18/4018; C08G 18/4808; C08G 18/6607; C08G 18/6674; C08G 18/6685; C08G 18/6692
See application file for complete search history.

(56) References Cited

U.S. PATENT DOCUMENTS

| | | | | |
|---|---|---|---|---|
| 5,554,673 | A * | 9/1996 | Shah | .......................... A61F 6/04 |
| | | | | 524/113 |
| 7,465,348 | B1 * | 12/2008 | Carlini | ................. C09D 11/101 |
| | | | | 106/31.62 |
| 2010/0258762 | A1 | 10/2010 | Isobe et al. | |
| 2012/0041145 | A1 | 2/2012 | Sommer et al. | |

FOREIGN PATENT DOCUMENTS

| | | | |
|---|---|---|---|
| CN | 102358777 A | | 2/2012 |
| CN | 103640133 A | * | 3/2014 |
| CN | 107236110 A | | 10/2017 |

(Continued)

OTHER PUBLICATIONS

Odian, G., Principles of Polymerization, Third Edition, John Wiley & Sons, Inc. 1991, pp. 19-24.*

(Continued)

*Primary Examiner* — Patrick D Niland
(74) *Attorney, Agent, or Firm* — Lerner David LLP

(57) ABSTRACT

Provided are a waterborne polyurethane emulsion for ultra-thin polyurethane condoms having a low modulus and a high strength, and a method for preparing the emulsion, wherein the waterborne polyurethane emulsion comprises 15 to 18 parts by mass of a macromolecular diol, 4 to 6 parts by mass of a diisocyanate, 0.6 to 0.9 parts by mass of a hydrophilic chain extender, 0.4 to 0.8 parts by mass of a small-molecule chain extender, and the like. The prepared waterborne polyurethane emulsion is characterized by a low modulus, a high strength, and high resilience.

17 Claims, 1 Drawing Sheet

(56)                    References Cited

FOREIGN PATENT DOCUMENTS

| | | | | |
|---|---|---|---|---|
| CN | 107266645 A | 10/2017 | | |
| CN | 111138614 A | 5/2020 | | |
| EP | 1447074 A2 * | 8/2004 | .............. | A61K 8/89 |
| EP | 3545040 A1 | 10/2019 | | |
| JP | 2013176257 | 1/2019 | | |
| WO | 2018057488 A1 | 3/2018 | | |

OTHER PUBLICATIONS

Machine English translation of CN 103640133, Chen, Mar. 19, 2014.*
International Search Report dated Mar. 16, 2021 issued in corresponding PCT international Application No. PCT/CN2020/137262.
Extended European Search Report dated Dec. 19, 2023 in EP20902064. 3, filed Dec. 17, 2020.

* cited by examiner

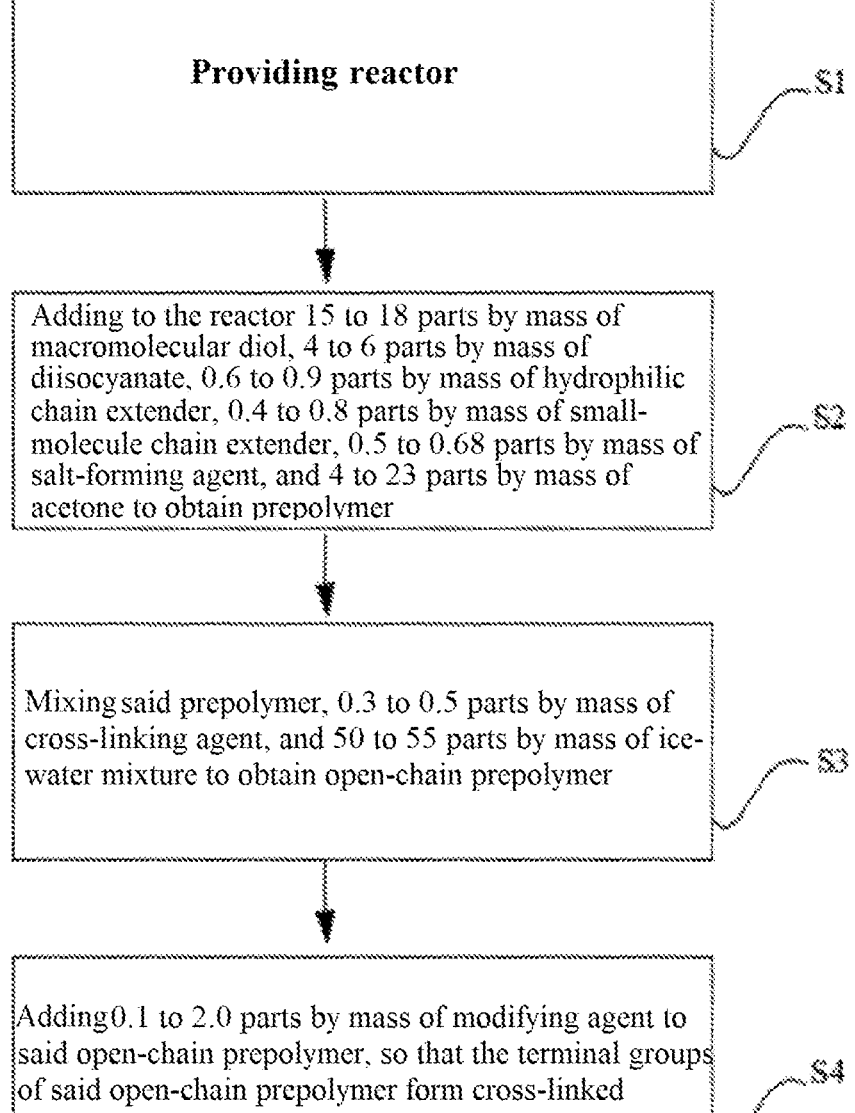

AQUEOUS POLYURETHANE EMULSION FOR ULTRA-THIN POLYURETHANE CONDOM WITH LOW MODULUS AND HIGH STRENGTH, AND PREPARATION METHOD THEREFOR

CROSS-REFERENCE TO RELATED APPLICATIONS

This application is a U.S. National Phase of International Patent Application No. PCT/CN2020/137262, filed on 17 Dec. 2020, which claims priority to Chinese Application Serial No. 201911320711.6 filed 19 Dec. 2019. The entire contents of these applications are incorporated herein by reference in their entirety.

TECHNICAL FIELD

The present invention relates to the field of polyurethane preparation, and specifically relates to a waterborne polyurethane emulsion for ultra-thin polyurethane condoms having a low modulus and a high strength, and a method for preparing the emulsion.

BACKGROUND ART

Current condoms are mainly prepared by using natural latex as the raw material, but the presence of water-soluble proteins in natural latex condoms can cause allergic reactions. Natural latex after a vulcanization process has residual nitrosamines, which have the potential to cause cancer. The thickness of condoms prepared with natural latex as the raw material is 36 μm or more, and such thickness causes a poor user experience. Natural latex condoms made 36 μm or thinner have the shortcomings of a poor strength and being easy to break during use.

Waterborne polyurethane condoms have been studied for more than a decade. Although some of such polyurethane condoms in the art meet the requirements on strength, the use of high boiling point solvents causes toxicity and these solvents are difficult to dry. Other waterborne polyurethane condoms prepared have a low bursting strength and a small maximum force, and are always at risk of rupturing during use. Therefore, there is a need for further improvement and optimization of the method for preparing a waterborne polyurethane emulsion required for preparation of waterborne polyurethane condoms, which are a hot research topic and also a difficult task in this field.

SUMMARY OF INVENTION

The present invention aims to provide a waterborne polyurethane emulsion for ultra-thin polyurethane condoms having a low modulus and a high strength, and a method for preparing the emulsion, so that the prepared waterborne polyurethane emulsion is characterized by a low modulus, a high strength, and high resilience, and overcomes the disadvantages of natural latex condoms such as water-soluble protein-induced allergy, existence of carcinogenic nitrosamines, a poor user experience due to a thick film, and a poor virus blocking performance.

To solve the above problems, the present invention is realized by the following technical solutions. The present invention provides a waterborne polyurethane emulsion, comprising:

15 to 18 parts by mass of a macromolecular diol, 4 to 6 parts by mass of a diisocyanate, 0.6 to 0.9 parts by mass of a hydrophilic chain extender, 0.4 to 0.8 parts by mass of a small-molecule chain extender, 0.5 to 0.68 parts by mass of a salt-forming agent, 0.3 to 0.5 parts by mass of a cross-linking agent, 0.1 to 2.0 parts by mass of a modifying agent, 50 to 55 parts by mass of an ice-water mixture, and 21 to 23 parts by mass of acetone;

wherein said modifying agent is a polyether substance that causes the terminal groups of the chain of the waterborne polyurethane molecule to form a cross-linked structure.

In one embodiment, said modifying agent is a polyetheramine.

In one embodiment, said cross-linking agent is a latent isocyanate-based cross-linking agent.

In one embodiment, said macromolecular diol is one of, or a combination of more of, polypropylene glycol, polytetrahydrofuran ether glycol, and poly(neopentyl glycol adipate).

In one embodiment, the molecular weight of said macromolecular diol is 2000 to 3000.

In one embodiment, said diisocyanate is one of, or a combination of more of, isophorone diisocyanate, hydrogenated diphenylmethane diisocyanate and/or hexamethylene diisocyanate.

In one embodiment, said waterborne polyurethane emulsion has a solid content of 30% to 32% and a pH of 6.5 to 7.5.

In one embodiment, said hydrophilic chain extender is dihydroxymethyl propionic acid and/or dihydroxymethyl butyric acid.

Another objective of the present invention is to provide a method for preparing a waterborne polyurethane emulsion, comprising at least the steps of providing a reactor;

adding to said reactor 15 to 18 parts by mass of a macromolecular diol, 4 to 6 parts by mass of a diisocyanate, 0.6 to 0.9 parts by mass of a hydrophilic chain extender, 0.4 to 0.8 parts by mass of a small-molecule chain extender, 0.5 to 0.68 parts by mass of a salt-forming agent, and 4 to 23 parts by mass of acetone, to obtain a prepolymer;

mixing said prepolymer, 0.3 to 0.5 parts by mass of a cross-linking agent, and 50 to 55 parts by mass of an ice-water mixture to obtain an open-chain prepolymer;

adding 0.1 to 2.0 parts by mass of a modifying agent to said open-chain prepolymer, so that the terminal groups of said open-chain prepolymer form a cross-linked structure, to obtain said waterborne polyurethane emulsion.

In one embodiment, said modifying agent is added dropwise to said open-chain prepolymer over a period of 25 to 35 minutes.

In one embodiment, said 21 to 23 parts by mass of acetone are added to said reactor in three portions.

In one embodiment, after the terminal groups of said open-chain prepolymer form a cross-linked structure, a solvent removing process is performed to remove the acetone.

Another objective of the present invention to provide use of the waterborne polyurethane emulsion in the field of polyurethane condoms.

The waterborne polyurethane emulsion prepared according to the present invention is characterized by a low modulus, a high strength, and high resilience, and waterborne polyurethane condoms prepared from the waterborne polyurethane emulsion according to the present invention are non-toxic, free of special odors, non-allergenic, dense, effective to block various viruses, and thinner, and have good thermal conductivity, a low modulus, a high strength, and a good user experience, thereby overcoming the disadvantages of natural latex condoms such as allergenicity of water-soluble proteins, presence of carcinogenic nitrosamines, a poor user experience due to a thick film, and a poor protection against viruses, and also overcoming the shortcomings of existing waterborne polyurethane condoms such as a high modulus, a low strength, and poor elongation. The waterborne polyurethane condoms prepared from the waterborne polyurethane emulsion in accordance with the method for preparing the waterborne polyurethane condom have a single-layer thickness as thin as 30 μm or less, a film elongation at break not less than 1000%, a breaking strength not less than 30 MPa, a 100% modulus not more than 1.8 MPa, a condom burst pressure more than 2.5 kPa, and a burst volume not less than 6 L.

DESCRIPTION OF DRAWINGS

FIG. 1 is a flowchart of the method according to an embodiment of the present invention.

DETAILED DESCRIPTION

The present invention is further described below with reference to several specific embodiments, but it should be noted that the specific material ratios, process conditions, and results described in the embodiments of the present invention are only for the purpose of illustrating the present invention, and are not to limit the scope of protection of the present invention. Any equivalent changes or modifications made according to the spirit of the present invention should be encompassed within the scope of protection of the present invention. Note that the "%" used in the description herein refers to "parts by mass", if not otherwise specified.

The present invention uses a polyetheramine as a post-chain extender, which causes the terminal groups of the chain of the waterborne polyurethane molecule to form a cross-linked structure, such that the prepared waterborne polyurethane emulsion is characterized by a low modulus, a high strength, and high resilience.

Referring to FIG. 1, a flowchart of a method for preparing a waterborne polyurethane emulsion in an embodiment of the present invention, the present invention provides a method for preparing a waterborne polyurethane emulsion, comprising at least the steps of

S1) providing a reactor;

S2) adding to said reactor 15 to 18 parts by mass of a macromolecular diol, 4 to 6 parts by mass of a diisocyanate, 0.6 to 0.9 parts by mass of a hydrophilic chain extender, 0.4 to 0.8 parts by mass of a small-molecule chain extender, 0.5 to 0.68 parts by mass of a salt-forming agent, and 4 to 23 parts by mass of acetone, to obtain a prepolymer;

S3) mixing said prepolymer, 0.3 to 0.5 parts by mass of a cross-linking agent, and 50 to 55 parts by mass of an ice-water mixture to obtain an open-chain prepolymer; and

S4) adding 0.1 to 2.0 parts by mass of a modifying agent to said open-chain prepolymer, so that the terminal groups of said open-chain prepolymer form a cross-linked structure to obtain said waterborne polyurethane emulsion.

In a specific embodiment, in step S1, the reactor is for example a reaction kettle.

In a specific embodiment, in step S2, 15%-18% of a macromolecular diol is put into a reactor, such as a reaction kettle, heated to 100-110° C. under stirring, dehydrated under vacuum at −0.1 MPa until the water content in the macromolecular diol is 0.03% or lower, and cooled to 35-40° C.; then 4%-6% of a diisocyanate is added, the temperature is elevated to 80-90° C. under stirring, and a reaction is allowed to proceed at this temperature for 2-3 hours and then cooled to 45-50° C.; 0.6%-0.9% of a hydrophilic chain extender and 7% of acetone are added, the temperature is elevated to 80° C. under stirring, and a reaction is allowed to proceed for 3-4 hours and then cooled to 50-55° C.; 0.4%-0.8% of a small-molecule chain extender and 4% of acetone are added, the temperature is elevated to 70-75° C. under stirring, and a reaction is allowed to proceed for 2-3 hours and then cooled to 10-20° C.; 0.5%-0.68% of a salt-forming agent and 10%-12% of acetone are added, followed by stirring for 30 minutes, to obtain a prepolymer. Herein, the macromolecular diol used is one or more of polypropylene glycol (PPG), polytetrahydrofuran ether glycol (PTMEG) and/or poly(neopentyl glycol adipate) (PNA). The molecular weight of the macromolecular diol is 2000-3000. If the molecular weight of the macromolecular diol is too large, the resilience and breaking strength of a film formed from the waterborne polyurethane emulsion will decrease. If the molecular weight is too small, the film formed from the waterborne polyurethane emulsion is easy to rupture, and has a large modulus. The diisocyanate used is one or more of isophorone diisocyanate (IPDI), hydrogenated diphenylmethane diisocyanate ($H_{12}$MDI) and/or hexamethylene diisocyanate (HDI). If an aromatic diisocyanate is selected, the film formed from the obtained waterborne polyurethane has a risk of yellowing. When the diisocyanate is IPDI or HDI, the reactivity of the isocyanate is low; and the reaction temperature of the diisocyanate and macromolecular diol in step S1 is 90° C. When the diisocyanate is $H_{12}$MDI, the reactivity of the diisocyanate is high, and the reaction temperature of the diisocyanate and macromolecular diol is 80° C. The hydrophilic chain extender used is dimethylol propionic acid (DMPA) and/or dimethylol butyric acid (DMBA). The small-molecule chain extender used is one or more of cyclohexanedimethanol (CHDM), 1,4-butanediol (BD) and/or methylpropanediol (MPD). In the present invention, the temperature is reduced to 35-40° C., 4%-6% of a diisocyanate is added, the temperature is elevated to 80-90° C. under stirring, and a reaction is allowed to proceed at this temperature for 2-3 hours and then cooled to 45-50° C.; 0.6%-0.9% of a hydrophilic chain extender and 7% of acetone are added, the temperature is elevated to 80° C. under stirring, and a reaction is allowed to proceed for 3-4 hours and then cooled to 50-55° C.; 0.4%-0.8% of a small-molecule chain extender and 4% of acetone are added, the temperature is elevated to 70-75° C. under stirring, and a reaction is allowed to proceed for 2-3 hours and then cooled to 10-20° C.; and 0.5%-0.68% of a salt-forming agent and 10%-12% of acetone are added, wherein the purpose of the three-stage cooling and feeding process is to make the chains of the waterborne polyurethane molecules more regular and to have a high degree of microphase separation, so as to improve the mechanical properties such as tensile strength of the prepared waterborne polyurethane.

Specifically, in step S3, the prepolymer is transferred to an emulsifying device, 0.3% to 0.5% of a cross-linking agent is added, the mixture is stirred at 300 rpm for 30-35 minutes, and 50% to 55% of the ice-water mixture is added at a constant rate to the prepolymer, under stirring at a high speed adjusted to 1000-1400 rpm.

Specifically, in step S4, after the prepolymer is opened, stirring is continued for 5 minutes; then the stirring speed is adjusted to 400 rpm, 0.1% to 2.0% of an aqueous solution of the modifying agent is added, and stirring is continued for 3 to 5 hours. The cross-linking agent used is a latent isocyanate cross-linking agent, such as any one of Tanatex latent isocyanate cross-linking agent ACRAFIX FAE and/or ACRAFIX FAX, and the crosslinking temperature of the latent cross-linking agent is 90-110° C. to ensure the stability of the waterborne polyurethane emulsion when stored at room temperature. The crosslinking occurs during the film formation of the waterborne polyurethane, which is favorable to fusion of particles and improvement in the polyurethane film performance. The modifying agent is for example a polyetheramine, which is a flexible curing agent and also serves as a post-chain extender in the present invention. When it serves as a post-chain extender, there is terminal-group cross-linking, which does not increase the modulus of the polyurethane film, while the cross-linked structure can increase the resilience and strength of the polyurethane film. In addition, according to the present invention, other post-chain extenders, such as ethylenediamine and isophorone diamine, may be additionally added. Ethylenediamine has a good symmetry, and as a post-chain extender it can provide a higher strength for the polyurethane film. Isophorone diamine contains an aliphatic six-membered ring structure in a "boat" and "chair" conformational transition, and as a post-chain extender it can improve the resilience of the polyurethane film. The emulsion obtained in step S4 was warmed up to 40-45° C., and acetone was removed from the emulsion at −0.09 MPa to produce a low-modulus, high-strength waterborne polyurethane emulsion. The solid content of the produced waterborne polyurethane emulsion is 30%-32%. The pH value of the produced waterborne polyurethane emulsion is 6.5-7.5.

In the present invention, for example, the polyetheramine and other post-chain extenders should be added slowly, over a controlled period of about 25 to 35 minutes. A too fast addition speed leads to serious local heat release and increases the degree of water involvement, resulting in an increased amount of urea bonds and an uneven molecular weight distribution in the obtained waterborne polyurethane molecules.

Some examples are given below to further illustrate the present invention. Some comparative examples are also provided, for example those using post-chain extenders such as ethylenediamine or isophorone diamine added for comparison with the polyether substances.

In one Example, 16%-16.67% of PTMEG 3000 was put into a reaction kettle, heated to 100-110° C. under stirring, and dehydrated under vacuum at −0.1 MPa until the water content in the macromolecular diol was 0.03% or lower. The temperature was decreased to 35-40° C., 4.16% of IPDI was added, and the mixture was heated to 90° C. under stirring to allow a reaction to proceed at this temperature for 2.5 hours. The temperature was decreased to 45-50° C., 0.67% of DMPA and 7% of acetone were added, and the mixture was heated up to 80° C. under stirring to allow a reaction to proceed for 3-4 hours. The temperature was decreased to 50-55° C., 0.73% of CHDM and 4% of acetone were added, and the mixture was heated to 75° C. under stirring to allow a reaction to proceed for 3-4 hours. Then the temperature was decreased to 15° C., 0.5% of a salt-forming agent and 10% of acetone were added, and the mixture was stirred for 30-35 minutes to obtain a first prepolymer. The first prepolymer was transferred to an emulsifying device, 0.3% of a cross-linking agent was added, and the mixture was stirred at 300 rpm for 30-35 minutes. Under stirring at a high speed adjusted to 1200 rpm, 53.32% of an ice-water mixture was added at a constant speed to the prepolymer to obtain the open chain first prepolymer. After the first prepolymer was opened, stirring was continued for 5-10 minutes, then the stirring speed was adjusted to 400 rpm, and 2.5%-2.65% of a polyetheramine was added dropwise over a controlled period of about 25-35 minutes. Then stirring was continued for 5-5.5 hours, the obtained emulsion was warmed up to 40-45° C., and acetone was removed from the emulsion under −0.09 MPa to produce Waterborne Polyurethane Emulsion A.

In another Example, 15.38% of PNA 2000 was put into a reaction kettle, heated to 100-110° C. under stirring, and dehydrated under vacuum at −0.1 MPa until the water content in the macromolecular diol was 0.03% or lower. The temperature was decreased to 35-40° C., 2.0% of IPDI and 2.0% of HDI were added, and the mixture was heated to 90° C. under stirring to allow a reaction to proceed at this temperature for 2.5 hours. The temperature was decreased to 45-50° C., 0.72% of DMPA and 7% of acetone were added, and the mixture was heated up to 80° C. under stirring to allow a reaction to proceed for 3-4 hours. The temperature was decreased to 50-55° C., 0.4% of BDO and 4% of acetone were added, and the mixture was heated to 75° C. under stirring to allow a reaction to proceed for 3-4 hours. Then the temperature was decreased to 15° C., 0.54% of a salt-forming agent and 12% of acetone were added, and the mixture was stirred for 30-35 minutes to obtain a second prepolymer. The second prepolymer was transferred to an emulsifying device, 0.3% of a cross-linking agent was added, and the mixture was stirred at 300 rpm for 30-35 minutes. Under stirring at a high speed adjusted to 1200 rpm, 53.5% of an ice-water mixture was added at a constant speed to the prepolymer to obtain the open chain second prepolymer. After the second prepolymer was opened, stirring was continued for 5-10 minutes, then the stirring speed was adjusted to 400 rpm, and 1.8%-2.0% of a polyetheramine was added dropwise over a controlled period of about 25-35 minutes. Then stirring was continued for 5-5.5 hours, the obtained emulsion was warmed up to 40-45° C., and acetone was removed from the emulsion under −0.09 MPa to produce Waterborne Polyurethane Emulsion B.

In one Comparative Example, 16.67% of PTMEG 3000 and PPG 3000 were put into a reaction kettle, heated to 100-110° C. under stirring, and dehydrated under vacuum at −0.1 MPa until the water content in the macromolecular diol was 0.03% or lower. The temperature was decreased to 35-40° C., 4.16% of IPDI was added, and the mixture was heated to 90° C. under stirring to allow a reaction to proceed at this temperature for 2.5 hours. The temperature was decreased to 45-50° C., 0.67% of DMPA and 7% of acetone were added, and the mixture was heated up to 80° C. under stirring to allow a reaction to proceed for 3-4 hours. The temperature was decreased to 50-55° C., 0.73% of CHDM and 4% of acetone were added, and the mixture was heated to 75° C. under stirring to allow a reaction to proceed for 3-4 hours. Then the temperature was decreased to 15° C., 0.5% of a salt-forming agent and 10.8% of acetone were added, and the mixture was stirred for 30 minutes to obtain a third prepolymer. The third prepolymer was transferred to an emulsifying device, 0.3% of a cross-linking agent was added, and the mixture was stirred at 300 rpm for 30-35 minutes. Under stirring at a high speed adjusted to 1200 rpm, 53.32% of an ice-water mixture was added at a constant speed to the prepolymer to obtain the open chain third prepolymer. After the third prepolymer was opened, stirring was continued for 5-10 minutes, then the stirring speed was adjusted to 400 rpm, and 1.5%-1.84% of an aqueous solution of isophorone diamine was added dropwise over a controlled period of about 25-35 minutes. Then stirring was continued for 3-3.5 hours, the obtained emulsion was warmed up to 40-45° C., and acetone was removed from the emulsion under −0.09 MPa to produce Waterborne Polyurethane Emulsion C.

In another Comparative Example, 16.07% of PPG 3000 were put into a reaction kettle, heated to 100-110° C. under stirring, and dehydrated under vacuum at −0.1 MPa until the water content in the macromolecular diol was 0.03% or lower. The temperature was decreased to 35-40° C., 3.27% of IPDI and 1.4% H$_{12}$MDI were added, and the mixture was heated to 80° C. under stirring to allow a reaction to proceed at this temperature for 2.5 hours. The temperature was decreased to 45-50° C., 0.82% of DMPA and 7% of acetone were added, and the mixture was heated up to 80° C. under stirring to allow a reaction to proceed for 3 hours. The

8 mold was cleaned and dried, then immersed into an emulsion of nanoscale (1 nm to 100 nm) waterborne polyurethane cross-linked particles, then removed out of the emulsion, and dried after dripping. The treated mold was immersed into a waterborne polyurethane emulsion, then removed out of the emulsion, and dried after dripping, and a waterborne polyurethane film was formed on the surface of the mold. The open end of the waterborne polyurethane film on the mold surface was rolled. The treated mold was immersed into hot water at 50±5° C., soaked and dried. Then the mold was dipped into a mold releasing agent, and was taken out and dried. The treated film was electrically tested by a dry method, and the mold was demolded after passing the electrical test, so that the polyurethane condom was obtained.

TABLE 1

| | Performance test results of condoms made from samples of Examples | | | | | | |
|---|---|---|---|---|---|---|---|
| Name of Sample | Single layer thickness/μm | 100% modules/Mpa | Max force/N | Breaking strength/ MPa | Elongation at break/% | Burst pressure/ kPa | Burst volume/L |
| Waterborne polyurethane emulsion A | 25 | 1.49 | 17.3 | 34.6 | 1074.34 | 2.5 | 10.4 |
| Waterborne polyurethane emulsion B | 25 | 1.60 | 19.6 | 37.7 | 1034.89 | 3.0 | 9.3 |
| Waterborne polyurethane emulsion C | 26 | 1.80 | 16.9 | 32.5 | 1002.35 | 2.2 | 7.7 |
| Waterborne polyurethane emulsion D | 26 | 1.73 | 15.8 | 30.38 | 1103.73 | 2.3 | 8.0 | temperature was decreased to 50-55° C., 0.75% of CHDM and 4% of acetone were added, and the mixture was heated to 75° C. under stirring to allow a reaction to proceed for 3 hours. Then the temperature was decreased to 10° C., 0.61% of a salt-forming agent and 12% of acetone were added, and the mixture was stirred for 30 minutes to obtain a fourth prepolymer. The fourth prepolymer was transferred to an emulsifying device, 0.5% of a cross-linking agent was added, and the mixture was stirred at 300 rpm for 30-35 minutes. Under stirring at a high speed adjusted to 1200 rpm, 53.43% of an ice-water mixture was added at a constant speed to the prepolymer to obtain the open chain fourth prepolymer. After the fourth prepolymer was opened, stirring was continued for 5 minutes, then the stirring speed was adjusted to 400 rpm, and 0.1%-0.15% of an aqueous solution of ethylenediamine was added dropwise over a controlled period of about 25-35 minutes. Then stirring was continued for 3-3.5 hours, the obtained emulsion was warmed up to 40-45° C., and acetone was removed from the emulsion under −0.09 MPa to produce Waterborne Polyurethane Emulsion D.

From the waterborne polyurethane emulsions prepared in the above Examples, polyurethane condoms were prepared according to the method for preparing waterborne polyurethane condoms disclosed in CN 103640133A, and the performance of the condoms was tested according to GB7544-1992, GB/T7546-1992 and GB/T7547-1992, with the test results shown in Table 1 below.

In the present invention, the prepared waterborne polyurethane emulsions were used to prepare waterborne polyurethane condoms by the following steps: a stainless steel From an analysis of the data in Table 1, it is concluded that the polyurethane condoms prepared from the waterborne polyurethane emulsions with a polyetheramine as the post-chain extender, have a higher overall performance than those with ethylenediamine and isophorone diamine as the post-chain extender. Polyetheramine is a flexible curing agent, and when it is used as a post-chain extender, there is terminal-group cross-linking, which on one hand does not increase the modulus of the polyurethane film, and on the other hand can increase the resilience and breaking strength of the polyurethane film.

The waterborne polyurethane emulsion prepared according to the present invention is characterized by a low modulus, a high strength, and high resilience, and waterborne polyurethane condoms prepared from the waterborne polyurethane emulsion according to the present invention are non-toxic, free of special odors, non-allergenic, dense, effective to block various viruses, and thinner, and have good thermal conductivity, a low modulus, a high strength, and a good user experience, thereby overcoming the disadvantages of natural latex condoms such as allergenicity of water-soluble proteins, presence of carcinogenic nitrosamines, a poor user experience due to a thick film, and a poor protection against viruses, and also overcoming the shortcomings of existing waterborne polyurethane condoms such as a high modulus, a low strength, and poor elongation. The waterborne polyurethane condoms prepared from the waterborne polyurethane emulsions in accordance with the method for preparing the waterborne polyurethane condom have a single-layer thickness as thin as 30 μm or less, a film elongation at break not less than 1000%, a breaking strength not less than 30 MPa, a 100% modulus not more than 1.8 MPa, a condom burst pressure more than 2.5 kPa, and a burst volume not less than 6 L.

The above embodiments are only preferred embodiments of the present invention, and are not intended to limit the present invention virtually or essentially. It should be understood that those ordinarily skilled in the art may make improvements and supplements that are also within the scope of the present invention, without departing from the method of the present invention. Those skilled in the art, without departing from the spirit and scope of the present invention, can use the above-disclosed technical contents to make changes, modifications and derived equivalents, all belonging to equivalent embodiments of the present invention. Furthermore, any equivalent changes, modifications, and derivations made to the above-mentioned embodiments according to the essential technology of the present invention still fall within the scope of the technical solutions of the present invention.

The invention claimed is:

1. A waterborne polyurethane emulsion, comprising:

15 to 18 parts by mass of a macromolecular diol selected from the group consisting of polypropylene glycol (PPG), polytetrahydrofuran ether glycol (PTMEG), poly(neopentyl glycol adipate) (PNA), and combinations thereof, 4 to 6 parts by mass of a diisocyanate, 0.6 to 0.9 parts by mass of a hydrophilic chain extender, 0.4 to 0.8 parts by mass of a small-molecule chain extender selected from the group consisting of cyclohexanedimethanol (CHDM), 1,4-butanediol (BD), methylpropanediol (MPD), and combinations thereof, 0.5 to 0.68 parts by mass of a salt-forming agent, 0.3 to 0.5 parts by mass of a cross-linking agent, 0.1 to 2.0 parts by mass of a modifying agent, 50 to 55 parts by mass of an ice-water mixture, and 21 to 23 parts by mass of acetone;

wherein said modifying agent is a polyether substance that causes the terminal groups of the chain of the waterborne polyurethane molecule to form a cross-linked structure.

2. The waterborne polyurethane emulsion according to claim 1, wherein said modifying agent is a polyetheramine.

3. The waterborne polyurethane emulsion according to claim 1, wherein said cross-linking agent is a latent isocyanate-based cross-linking agent.

4. The waterborne polyurethane emulsion according to claim 1, wherein said macromolecular diol is one of or a combination of more of polypropylene glycol, polytetrahydrofuran ether glycol, and poly(neopentyl glycol adipate).

5. The waterborne polyurethane emulsion according to claim 1, wherein said diisocyanate is selected from the group consisting of isophorone diisocyanate, hydrogenated diphenylmethane diisocyanate, hexamethylene diisocyanate, and combinations thereof.

6. The waterborne polyurethane emulsion according to claim 1, wherein said hydrophilic chain extender is dihydroxymethyl propionic acid and/or dihydroxymethyl butyric acid.

7. A method for preparing a waterborne polyurethane emulsion, comprising at least the following steps:

providing a reactor;

adding to said reactor 15 to 18 parts by mass of a macromolecular diol selected from the group consisting of polypropylene glycol (PPG), polytetrahydrofuran ether glycol (PTMEG), poly(neopentyl glycol adipate) (PNA), and combinations thereof, 4 to 6 parts by mass of a diisocyanate, 0.6 to 0.9 parts by mass of a hydrophilic chain extender, 0.4 to 0.8 parts by mass of a small-molecule chain extender, 0.5 to 0.68 parts by mass of a salt-forming agent, and 4 to 23 parts by mass of acetone to obtain a prepolymer, and wherein the small-molecule chain extender is selected from the group consisting of cyclohexanedimethanol (CHDM), 1,4-butanediol (BD), methylpropanediol (MPD), and combinations thereof;

mixing said prepolymer, 0.3 to 0.5 parts by mass of a cross-linking agent, and 50 to 55 parts by mass of an ice-water mixture to obtain an open-chain prepolymer; and adding 0.1 to 2.0 parts by mass of a modifying agent to said open-chain prepolymer, so that the terminal groups of said open-chain prepolymer form a cross-linked structure to obtain said waterborne polyurethane emulsion, and wherein the modifying agent is a polyether substance.

8. The waterborne polyurethane emulsion according to claim 7, wherein said modifying agent is added dropwise to said open-chain prepolymer over a period of 25 to 35 minutes.

9. A method of using the waterborne polyurethane emulsion according to claim 1 to manufacture polyurethane condoms, the method comprising:

treating a mold by immersing the mold in an emulsion of nanoscale waterborne polyurethane cross-linked particles;

drying the treated mold;

immersing the treated mold in the waterborne polyurethane emulsion;

drying the mold to produce a waterborne polyurethane film formed on the surface of the mold;

rolling an open end of the waterborne polyurethane film;

immersing the mold in water at 50±5° C.;

soaking and drying the mold;

dipping the mold into a mold release agent; and demolding the waterborne polyurethane film.

10. The method according to claim 7, wherein said modifying agent is a polyetheramine.

11. The method according to claim 7, wherein said cross-linking agent is a latent isocyanate-based cross-linking agent.

12. The method according to claim 7, wherein said diisocyanate is selected from the group consisting of isophorone diisocyanate, hydrogenated diphenylmethane diisocyanate, hexamethylene diisocyanate, and combinations thereof.

13. The method according to claim 7, wherein said hydrophilic chain extender is dihydroxymethyl propionic acid and/or dihydroxymethyl butyric acid.

14. The method according to claim 9, wherein said modifying agent is a polyetheramine.

15. The method according to claim 9, wherein said cross-linking agent is a latent isocyanate-based cross-linking agent.

16. The method according to claim 9, wherein said diisocyanate is selected from the group consisting of isophorone diisocyanate, hydrogenated diphenylmethane diisocyanate, hexamethylene diisocyanate, and combinations thereof.

17. The method according to claim 9, wherein said hydrophilic chain extender is dihydroxymethyl propionic acid and/or dihydroxymethyl butyric acid.

* * * * *